United States Patent
Schmitt-Walter et al.

(10) Patent No.: US 8,297,133 B2
(45) Date of Patent: Oct. 30, 2012

(54) PRESSURE SENSOR

(75) Inventors: Stefan Schmitt-Walter, Oberhaching (DE); Lutz Seffner, Dresden (DE); Thomas Roedig, Dresden (DE); Sylvia Gebhardt, Dresden (DE); Bent Brueckner, Dresden (DE); Andreas Schoenecker, Freital (DE)

(73) Assignees: S.W.A.C. Schmitt-Walter Automation Consult GmbH, Oberhaching (DE); Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 737 days.

(21) Appl. No.: 11/922,478

(22) PCT Filed: Jun. 20, 2005

(86) PCT No.: PCT/EP2005/006629
§ 371 (c)(1),
(2), (4) Date: Aug. 24, 2009

(87) PCT Pub. No.: WO2006/136182
PCT Pub. Date: Dec. 28, 2006

(65) Prior Publication Data
US 2010/0011884 A1 Jan. 21, 2010

(51) Int. Cl.
*G01L 1/10* (2006.01)
(52) U.S. Cl. .................................................. 73/862.625
(58) Field of Classification Search .............. 73/862.625
See application file for complete search history.

(56) References Cited

U.S. PATENT DOCUMENTS

| | | | | |
|---|---|---|---|---|
| 3,281,612 A | * | 10/1966 | Hatschek | 310/338 |
| 3,614,488 A | | 10/1971 | Sonderegger et al. | |
| 3,922,572 A | * | 11/1975 | Cook et al. | 310/334 |
| 4,510,412 A | * | 4/1985 | Suda et al. | 310/328 |
| 4,712,036 A | * | 12/1987 | Gurich | 310/333 |
| 4,802,371 A | * | 2/1989 | Calderara et al. | 73/862.043 |
| 5,265,481 A | * | 11/1993 | Sonderegger et al. | 73/862.625 |
| 5,376,857 A | * | 12/1994 | Takeuchi et al. | 310/328 |

FOREIGN PATENT DOCUMENTS

DE 1 236 827 B 3/1967

(Continued)

OTHER PUBLICATIONS

International Search Report dated Jan. 30, 2006.

(Continued)

*Primary Examiner* — Lisa Caputo
*Assistant Examiner* — Octavia Davis-Hollington
(74) *Attorney, Agent, or Firm* — Flynn, Thiel, Boutell & Tanis, P.C.

(57) ABSTRACT

A pressure sensor has a multiplicity of piezoelectric converter elements which are arranged such that they are essentially parallel to a force-applying or pressure-applying direction. The converter elements can be arranged at a distance from one another by an insulating material and/or are at least partially embedded in the material.

A support material having greater mechanical rigidity than the converter elements, in particular in the force-applying or pressure-applying direction, is assigned to at least a number of piezoelectric converter elements, or the piezoelectric converter element is applied, in the form of a layer, to a supporting body made from this support material and is electrically contact-connected, for example, by a bottom electrode, which is arranged between the converter element layer and the supporting body, and a cover electrode which is applied to an outer side of the converter element layer.

31 Claims, 4 Drawing Sheets

FOREIGN PATENT DOCUMENTS

| | | |
|---|---|---|
| DE | 103 36 357 A1 | 3/2005 |
| GB | 1 054 081 A | 1/1967 |
| JP | SHO60-073986 | 8/1986 |
| JP | HEI01-150829 A | 6/1989 |
| JP | HEI02-083424 A | 3/1990 |
| JP | HEI04-012741 | 3/1993 |
| JP | HEI08-313378 A | 11/1996 |

OTHER PUBLICATIONS

English translation of Office Action of Japanese Patent Office issued in Japanese Application No. 2008-517325 dated Dec. 21, 2010 (9 pages).

* cited by examiner

PRESSURE SENSOR

BACKGROUND OF THE INVENTION

Pressure sensors of the type mentioned at the beginning have also been used in recent times as, e.g., fingerprint sensors. Each of the multiplicity of piezoelectric converter elements is essentially rod-shaped and arranged at a distance from the others and parallel to them. The converter elements are embedded in an insulating material, whereby the free ends of the converter elements are electrically contact-connected. The contact-connection in this association is, as a rule, effected in the manner that each converter element can be separately electrically polled, so that there results a resolution by the corresponding pressure sensor of the exertion of pressure or force that is on an order of magnitude of 500 or more dpi (dots per inch).

The corresponding piezoelectric converter elements thereby generate a surface charge as a result of the corresponding piezoelectric effect, whereby there is essentially a linear relationship between the charge quantity and the deformation of the converter element.

Although such a known pressure sensor is well-suited for use as a fingerprint sensor, it shows, however, low resistivity to high pressures or a stability that is inadequate over the service life to allow use in highly precise mechanical applications with high pressures and over a long time. Were such a pressure sensor to be used, for example, in a bearing that is exactly guided with a high bias pressure, its shrinking would serve to cancel out the bias forces up to the point of absolute, free mobility of the mechanical components, so that this known sensor cannot be used at all for such a purpose.

SUMMARY OF THE INVENTION

For this reason, the invention takes as a basis the object of improving a pressure sensor of the type mentioned at the beginning to the effect that it can also be used for high pressures, for a long service life and for various mechanical applications.

According to an aspect of the invention, not only is an arrangement of insulating material, for example, between the piezoelectric converter elements, effected in order to arrange these at a distance from one another, a support material is additionally assigned to at least a number of converter elements, whereby this support material has, particularly in the pressure-applying or force-applying direction, greater mechanical rigidity than do the converter elements. There can also be analogously an assignment of at least one converter element layer to a supporting body made from the support material.

In this way, the corresponding converter element is prevented from being too strongly deformed under the influence of a greater mechanical load, so that the corresponding pressure sensor also has greater resistivity to high pressures. As a result of the support material, the service life of the pressure sensor is furthermore increased and a corresponding shrinking when a high bias pressure is used is prevented as far as possible.

The corresponding converter elements can have a circular, rectangular, particularly square, or oval cross-section, or even another cross-section. The corresponding converter elements can be arranged next to one another, whereby their distribution can be uniform or even non-uniform, depending on the requirement. Consequently, it is also possible, for example, for areas to be provided with converter elements in a greater density than that in other areas.

In order for it to be possible to arrange the corresponding converter elements next to one another in a simple manner, a matrix-like arrangement can be preferred. This can be formed from various rows and columns of converter elements.

Various insulating materials can be considered for the insulating material, whereby such materials can be polymer material, glass or even composite systems, such as layers sintered on to the supporting material, whereby it is possible for said insulating material to be formed as a matrix polymer, particularly in the case of the matrix-like arrangement of the converter elements.

In order to have a support material with sufficient high rigidity, this support material can be a ceramic material or a hard metal. For example, aluminium oxide or aluminium nitride can be used as such a ceramic material.

The electrical contact-connection of the corresponding converter elements depends on the required resolution of the pressure sensor. The resolution can theoretically amount to a few 100 dpi (dots per inch) as for the fingerprint sensor, whereby a corresponding distance between adjacent piezoelectric converter elements amounts to several tens of μm in this connection. In the case of lower resolution, there is likewise the possibility of contact-connecting converter elements for determining the corresponding surface charges on the upper and lower sides in groups, or of contact-connecting all converter elements together.

The contact-connecting in this connection can be produced over the corresponding end surfaces of the converter elements, which extend essentially perpendicularly to the force-applying or pressure-applying direction.

One type of such electrical contact-connection can preferably be formed as an electrically conductive coating in the form of strip conductors. This electrically conductive coating consists of a metal such as copper, silver, gold or aluminium.

In another embodiment, such electrical contact-connecting can also be formed as a material that is suitable for application and that contains electrically conductive particles (conductive paste).

There are a number of possibilities for combining the converter elements with the corresponding support material.

In one embodiment, the support material has a number of support tubes, each of which can hold an essentially rod-shaped converter element in a bore hole. As a rule, these have a centred bore hole into which the corresponding converter element is inserted. At the same time, this bore hole can be open at both ends, in order to contact-connect the converter elements via the end surfaces. There is, however, also the possibility of contact-connecting the corresponding converter element through a wall of the support tube.

A further possibility can be seen in the support material having a number of support rings, each of which can hold an essentially tube-shaped converter element. These have a certain length that essentially corresponds to the length of the converter elements, where these are arranged in the annular gap of the support rings.

Such a corresponding support ring can furthermore also have a centred bore hole. If necessary, a corresponding converter element with a rod-shape or the like is also arranged in this centred bore hole.

A further embodiment for a support material can be characterised by the fact that it has a number of support plate pairs, whereby each pair can hold an essentially plate-shaped converter element between the members of the pair. The corresponding dimensions of such a support plate pair can be the same in the lengthwise direction and in the transverse direction as those of the converter element. There is, however, also the possibility of having the converter element stick out beyond the support material in the form of a plate, particularly in the direction perpendicular to the pressure-applying or force-applying direction.

For simplified production of such a corresponding pressure sensor, the converter element and associated support material can form a composite material, together with the insulating material. Such composite materials can, for example, be used on all pressure-sensitive material connections, such as, for example, on steel constructions that require precise frictional connections. Today these are usually monitored in a very imprecise approximation via the starting torque of the screwed connection. This torque, however, is dependent upon the frictional coefficient and the exact surface below the screwed connection, and can vary by more than 20%. While there is also a possibility of monitoring the material connection by means of the linear stretching of the screw, design problems usually stand in the way of such a method, however, because often the two ends of such a screw are not both exposed for measurement.

According to the invention, it is possible, for example, in the case of pressure sensors with a disc-like or washer-like shape, for such a disc to remain in the construction. Such discs, especially those made of a composite material, can be economically manufactured. During tightening, they help in the exact evaluation of the applied pressure torques and consequently the exact measurement of the frictional connection. For this purpose, electronic evaluation devices are temporarily connected via the electrical contact-connection and then removed from the corresponding contact points after the measurement. These can be realised in various ways.

In order to optimise the pressure measurement, it is possible to arrange all converter elements uniaxially, together with the assigned support material.

Depending on the arrangement of the converter elements and support material, there are various possibilities for surrounding these with the insulating material or connecting them by means of it. In one embodiment, the converter elements and the assigned support material can be cast with the insulating material. This particularly applies to matrix-like arrangements of converter elements and support material.

A corresponding insulating material can also be arranged as an adhesive between the converter elements and the support material (see the above embodiments), for example, in connection with a plate-shaped support material and a plate-shaped converter element. Casting with the insulating material can still take place in addition.

It has already been pointed out that the support material should have greater mechanical rigidity than does the converter element. This can, for example, be realised by means of the modulus of elasticity of the support material being greater than the modulus of elasticity of the converter element and, as a rule, also that of the insulating material, or that the product of the modulus of elasticity and the area of the support material is very much greater than the product of the modulus of elasticity and the area of the converter element.

For electrical decoupling of adjacent converter elements, it can additionally be viewed as advantageous if a corresponding insulating resistance of the support material is greater than the insulating resistance of the converter element.

By means of the contact-connection of individual converter elements or groups of converter elements, it is possible to determine the high-sensitivity resolution of the pressure measurement. In order to be able to determine whether moments of tilt or torsional moments arise when there is, for example, a load and a mechanical connection, the pressure sensor can be divided into pressure measuring sectors in a plane perpendicular to the force-applying or pressure-applying direction.

If the corresponding pressure sensor is formed, for example, as a disc or washer, it can furthermore be advantageous in this connection if the pressure measuring sectors are in the form of circular segments arranged around a centre axis of the pressure sensor, said centre axis being parallel to the force-applying or pressure-applying direction. At the same time, it can furthermore be seen as favourable if each of these pressure measuring sectors extends across the same centre point angle relative to the centre axis.

There is the possibility that, in principle, support material with a specific shape is assigned to each converter element, see, for example, the ring and tube according to the above embodiments. There is, however, likewise the possibility that the support material is a solid material that has a multiplicity of corresponding receptacles, each one for one converter element with additional insulating material, where appropriate. In this connection, the insulating material can exercise an adhesive function.

In order to reach a greater charge effect using the converter elements, these can be formed from a ferroelectric piezoelectric material, such as lead-zirconate-lead-titanate, barium titanate or the like.

Instead of using a multiplicity of individual piezoelectric converter elements made of fibres, small rods or the like, there is, according to the invention, likewise the possibility of forming at least one piezoelectric converter element as a converter element layer that is applied to a supporting body made of the support material. For the electrical contact-connecting in this case, a bottom electrode is arranged between the converter element layer and the supporting body and a cover electrode is arranged on an outer side of the converter element layer, said outer side facing away from the supporting body.

This embodiment also results in the corresponding advantages with the support material that is formed with greater mechanical rigidity than the converter element layer, particularly in the force-applying or pressure-applying direction.

If a solid body is used as the supporting body, the corresponding converter element layer can be applied to its side surface or surfaces, whereby the converter element layer does not have to extend across the entire supporting body. It is likewise possible for the converter element layer to be applied to this outer side only at certain points in the circumferential direction of the supporting body, whereby the corresponding bottom and cover electrodes can likewise be formed only in places. Both the converter element layer and the bottom and cover electrodes can be formed as thin or thick layers.

In the case of a hollow supporting body, a corresponding converter element layer with electrodes can also be applied, either alternatively or together with a corresponding converter element layer on the outer side, to an inner side of the supporting body. Corresponding supporting bodies can have a round, oval or angular cross-section, as well as a square, rectangular or even polygonal one.

In order to be able to exert a force directly on the converter element layer, these can extend up to the upper and/or lower side of the corresponding supporting body. In this way, one end of the converter element layer lies free, or even both ends also lie free, so that pressure or a force can be exercised directly on this free end or these free ends.

In another embodiment, the corresponding converter element layer is arranged in a recess on the outer and/or inner side of the supporting body, so that the upper and lower ends of the layer are covered by the supporting body.

The contact-connection of the connector element layer is produced by means of bottom and cover electrodes, for example, in such a way that the polarisation direction is perpendicular to the force-applying or pressure-applying direction, whereby this means that the corresponding contact-connection between the layers is parallel to this force-applying or pressure-applying direction.

BRIEF DESCRIPTION OF THE DRAWINGS

In the following, advantageous embodiments of the invention are explained in more detail using the figures included with the drawing. Shown are.

DETAILED DESCRIPTION OF PREFERRED EMBODIMENTS

Figure 1:
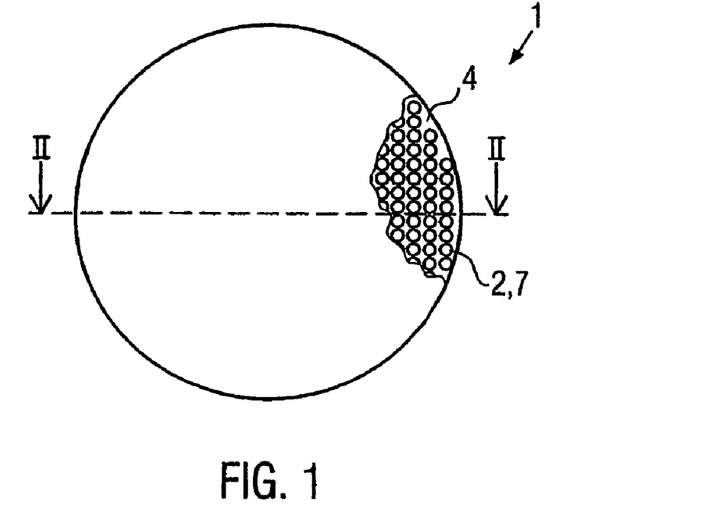
FIG. 1 illustrates a partially cut top view on to a first embodiment of a pressure sensor according to the invention.

FIG. 1 shows a top view on to a partially cut, disc-shaped pressure sensor 1 according to a first embodiment. The upper side of the pressure sensor 1 is given an electrical contact-connection for a multiplicity of converter elements 2 arranged in rows and columns. A support material 7 is assigned to each of the converter elements 2. The converter elements 2 and the assigned support material 7 are arranged at a distance to one another by means of an insulating material 4 and cast with the insulating material 4. The electrical contact-connection is likewise formed on a bottom side of the pressure sensor 1, in order, by means of the two electrical contact-connections, to derive the surface charges generated by an exerted pressure or an exercised force by means of the piezoelectric effect, from the corresponding piezoelectric converter elements 2 and to convert this into information on the applied pressure or the exerted force by means of a corresponding processing device. A display device for the measured pressure or force is not shown in FIG. 1 for reasons of simplification.

The corresponding converter elements 2 are preferably made from a ferroelectric piezoelectric material, such as lead zirconate-lead-titanate, barium titanate or the like. The assigned support material 7 is formed from a ceramic material or a hard metal. Corresponding ceramic materials are, for example, aluminium oxide or aluminium nitride and the like.

The insulating material 4 is a polymer material that serves both to cast the converter elements 2 with the support material 7 and to connect these two.

Figure 2:
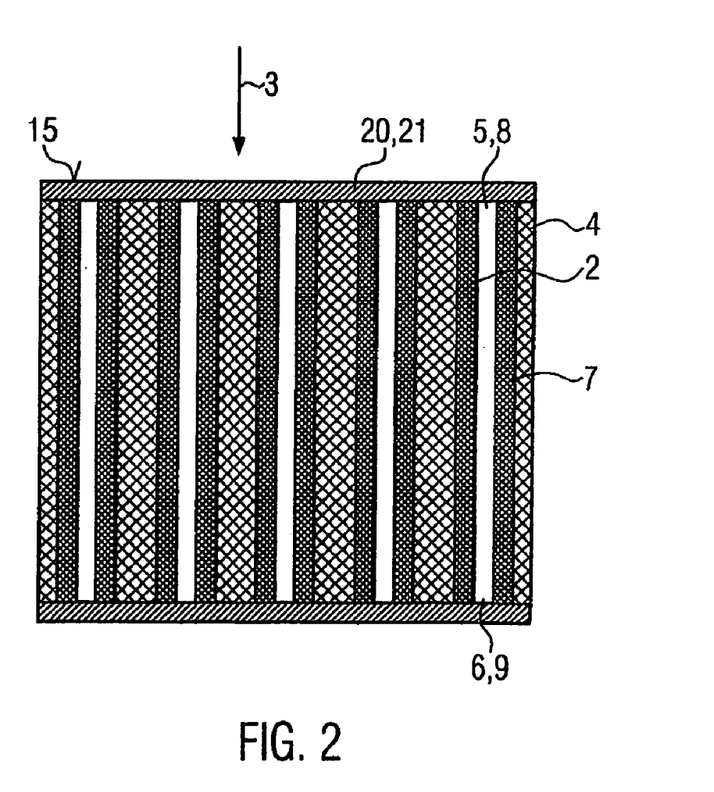
FIG. 2 illustrates a cut along the line II—II from FIG. 1.

FIG. 2 depicts a cut along the line II-II from FIG. 1. In this figure, and in all remaining figures, the same reference numbers are used for parts that are the same.

In FIG. 2, the adjacent arrangement of a multiplicity of converter elements 2 can be discerned, whereby each of these converter elements 2 is surrounded by the corresponding support material 7 in a tube shape. The converter elements 2 have a rod-like shape, whereby they can have a round, oval or also angular cross-section, particularly a rectangular one.

Upper and lower ends 5, 6 of the corresponding converter elements 2 are exposed on their end surfaces 8, 9 and are arranged so as to be essentially perpendicular to a pressure-applying or force-applying direction 3 in a plane 15. At the upper and lower ends of the converter elements 2, these are connected in this plane with an electrical contact-connection, which can be formed, for example, from an electrically conductive coating made of a metal such as copper, silver, gold or aluminium or from a material, such as a conductive paste, containing electrically conductive metal particles. The electrically conductive coating 20 is applied in the form of strip conductors 21. The corresponding strip conductors 21 are connected to the processing device (not shown) that detects the generated surface charges and converts them into a pressure level or force level.

Figure 3:
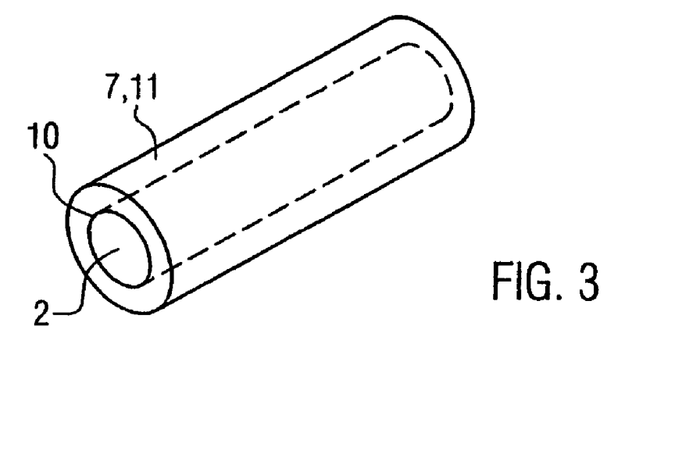
FIG. 3 illustrates an embodiment of a piezoelectric converter element with support material.
Figure 4:
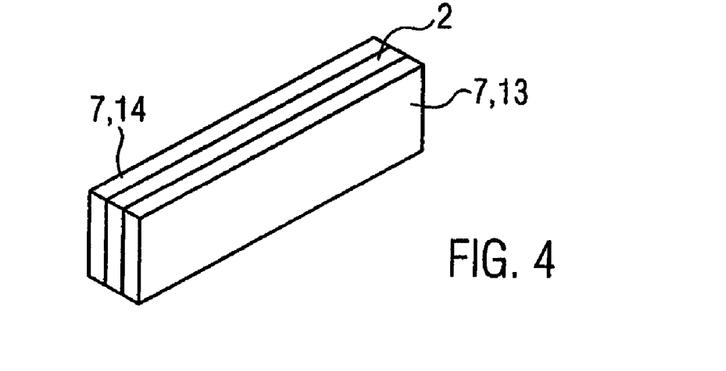
FIG. 4 illustrates a further embodiment of a piezoelectric converter element with support material.
Figure 5:
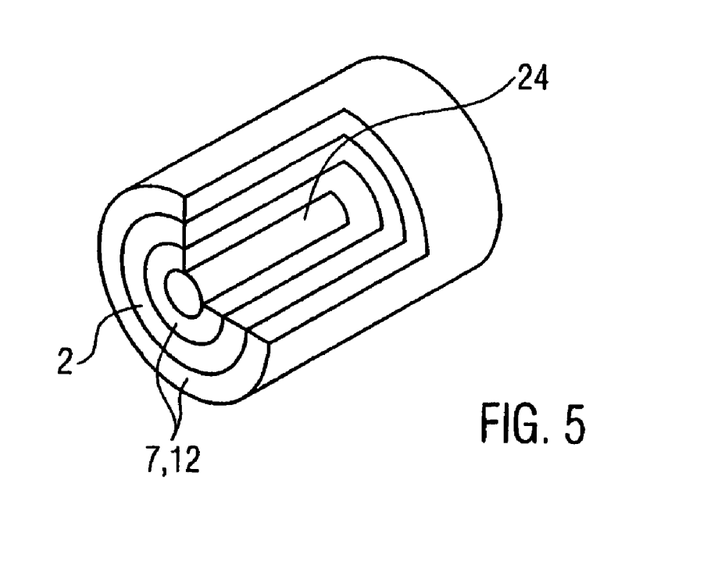
FIG. 5 illustrates a still further embodiment of a piezoelectric converter element with support material.

FIGS. 3 to 5 depict various embodiments for a converter element 2 with assigned support material 7. The embodiment according to FIG. 3 is, for example, used with the pressure sensor according to FIGS. 1 and 2. In this case, the support material 7 has the shape of a support tube 11 into whose centre bore hole 10 a rod-shaped converter element 2 is inserted.

In FIG. 4, two support plates 13, 14 are arranged, one on either side of a plate-shaped converter element 2. The dimensions of the plate-shaped converter element 2 in the lengthwise direction and also in the transverse direction correspond to those of the support plates 13, 14. An electrical contact-connection is produced on the ends of the plate-shaped converter element 2 that lie in the lengthwise direction; this is not shown in FIG. 4 for reasons of simplification.

In FIG. 5, in a further embodiment, the converter element 2 is essentially tube-shaped and inserted into an annular gap of a support ring 12 as support material 7. A central bore hole 24 is formed in the centre of the support ring 12 to save material or to hold a further converter element.

The elements shown in FIGS. 3 to 5 can, in accordance with FIG. 2, be next to one another in the form of a matrix and can be uniaxially aligned, whereby the insulating material 4 can serve both to cast the different elements and to connect, for example, the plate-shaped converter element 2 to the support plates 13 and 14 in FIG. 4.

The electrical contact-connection is essentially brought about in each case in a manner analogous to the one shown in FIG. 2. The arrangement of the different elements can be produced in a pressure sensor 1 according to FIG. 1, said pressure sensor 1 having an essentially circular cross-section. Other cross-section shapes, such as oval, polygonal and the like, are naturally possible for the pressure sensor 1.

Figure 6:
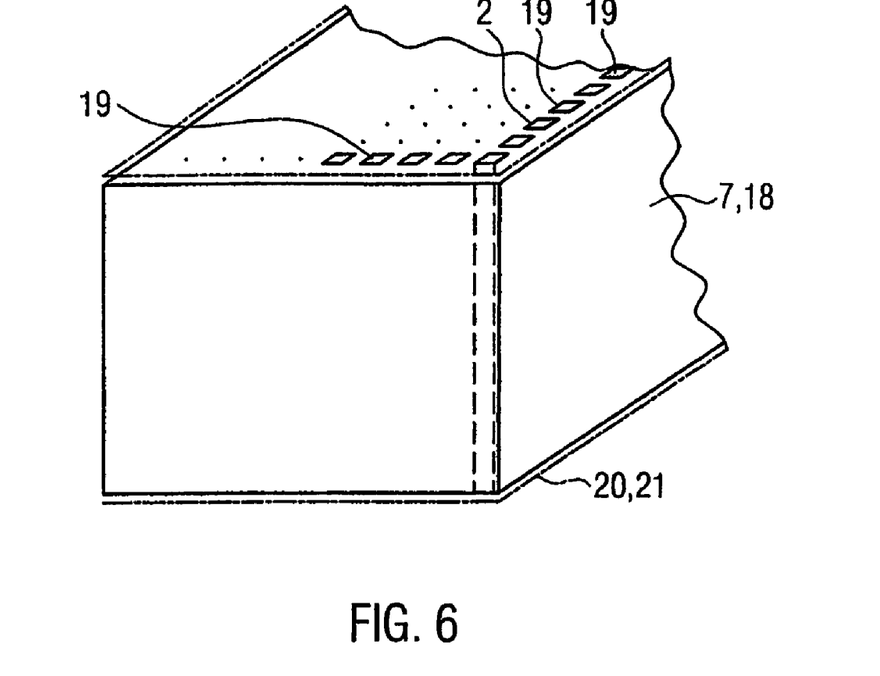
FIG. 6 illustrates a support material as solid material.

In FIG. 6, the support material 7 is formed as a solid material 18, for example, with a cuboid shape. This solid material 18 has a multiplicity of receptacles 19. These have a cross-section corresponding to that of the converter elements 2 that are inserted into these receptacles 19. In this case, a corresponding insulating material 4 is no longer necessary for casting or for maintaining a distance between the corresponding converter elements; instead, it can serve as an adhesive for joining the converter elements 2 to the walls of the receptacles 19 in the solid material 18. The electrical contact-connection is brought about in accordance with FIG. 2 by means of a coating 20 in the form of strip conductors 21 on the upper and lower end surfaces 8, 9 of the corresponding converter elements 2.

In this case, other cross-section shapes are again possible for the solid material 18 and/or the receptacles 19, depending on the intended use.

Figure 7:
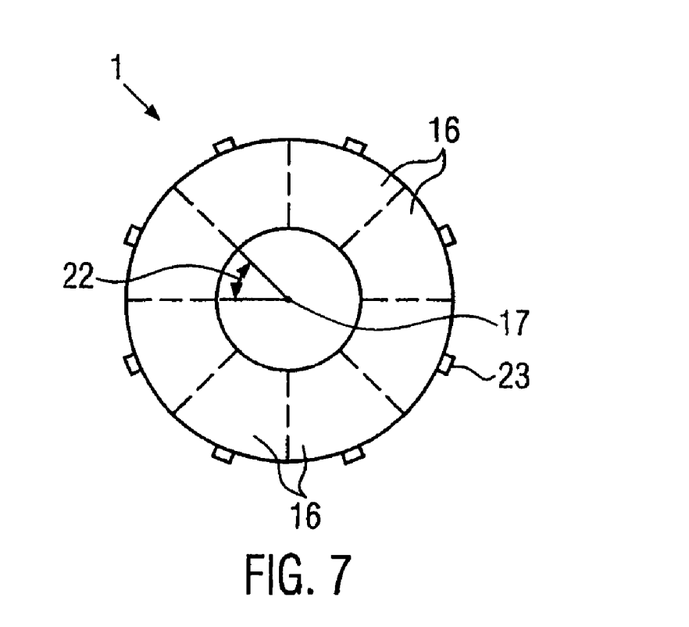
FIG. 7 illustrates a top view analogous to FIG. 1 on to a ring-shaped pressure sensor divided into sectors.

FIG. 7 depicts a further embodiment of a pressure sensor 1 that, in this case, is formed as a perforated disc or washer. In contrast to the pressure sensor 1 according to FIG. 1, the converter elements 2 are divided into pressure measuring sectors 16. Each of these pressure measuring sectors 16 has its own electrical contact-connection (see the various electrical connecting contacts 23). Each of the pressure measuring sectors 16 extends in the circumferential direction of the pressure sensor 1 over an equal centre point angle 22 relative to a centre axis 17, which runs parallel to the force-applying or pressure-applying direction 3 shown in FIG. 2. In the case of the depicted embodiment, the centre point angle is 45°.

In the case of a pressure sensor 1 according to FIG. 1, such a division into pressure measuring sectors 16 is also possible, whereby these then essentially extend to the centre axis 17, so that they form sectors of a circle.

As a result of the arrangement of such pressure measuring sectors 16, it is possible both to determine a total force or a total pressure by using all pressure measuring sectors 16 and furthermore to resolve this total pressure or total force relative to the centre axis 17 as a function of the angle. In this way, tilt or torsional moments relative to the force-applying or pressure-applying direction 3 can be determined.

Figure 8:
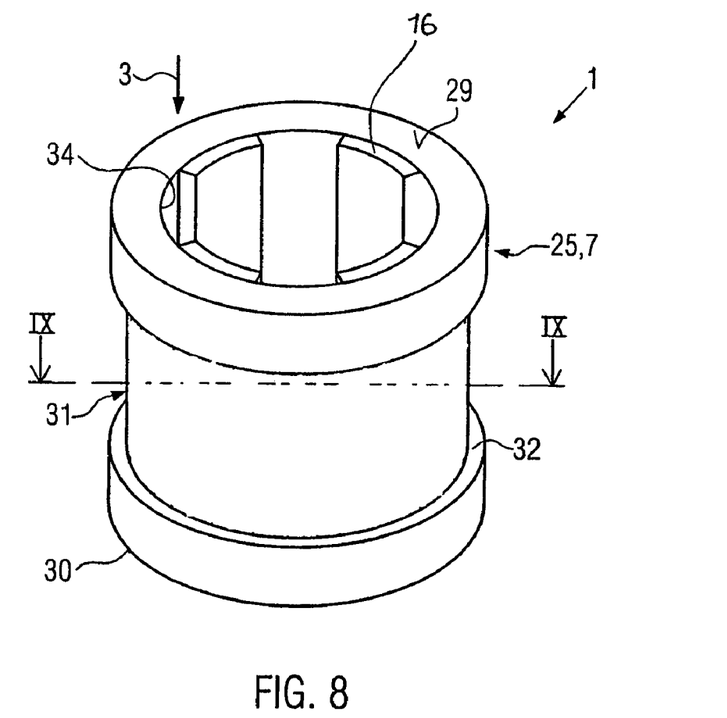
FIG. 8 illustrates a perspective side-view of a further embodiment.

FIG. 8 shows a perspective side-view of a further embodiment of a pressure sensor 1 according to the invention. This differs from the previously described embodiments particularly in that instead of a multiplicity or multiple number of piezoelectric converter elements, a corresponding converter element layer 26 is applied to a supporting body 25 made from the support material 7. For the electrical contact-connection, one or more bottom electrodes 27 are applied, likewise in layered form, between the converter element layer 26 and an outer side of the supporting body 25, and one or more cover electrodes 28 are applied, likewise in layered form, on an outer side of the converter element layer 26. As a result, there is polarization in the direction perpendicular to the force-applying or pressure-applying direction 3. The corresponding layers can be formed as thin or thick layers. The materials for the layers here correspond to the materials described in the case of the preceding embodiments.

In the case of the embodiment according to FIG. 8, a corresponding converter element layer 26 is applied along the entire circumference of the supporting body 25 on its outer side, while the converter element layer 26 is applied on a corresponding inner side 34 only across certain angles at circumference 35. In the depicted example, each converter element layer section 26 extends across a centre point angle of approximately 45° and adjacent converter element layer sections are spaced apart from one another by a centre point angle of likewise approximately 45°.

The bottom or cover electrode can likewise be formed in a manner analogous to the converter element layer sections. The converter element layer 26 on the outer side of the supporting body 25 is arranged in a recess 30 that is essentially ring-shaped, so that the upper and lower ends of the layer 26 are covered by an overhang 32 of the supporting body 25. In another embodiment, however, it can be that the converter element layer 26 extends up to an upper side 29 and/or lower side 30 of the supporting body 25 (also refer to the converter element layer sections 26 applied to the inner side 34 in this regard).

The geometric shape of the supporting body 25 is only by way of example, whereby other geometric forms, such as cubes, cuboids or the like can also be used, each also with corresponding inner bore hole and associated inner side 34, where appropriate. Likewise, it is possible that the supporting body 35 is formed from a solid material, so that a corresponding converter element layer 26 is applied only to an outer side of this supporting body.

Figure 9:
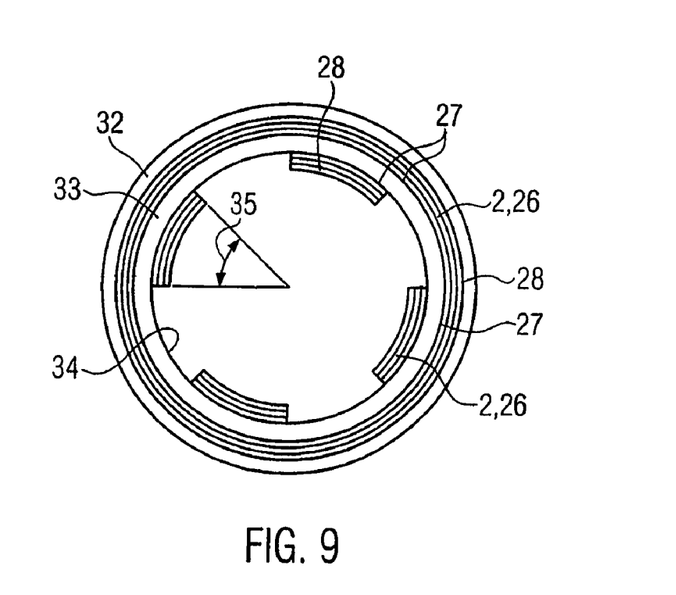
FIG. 9 illustrates a cut along the line IX—IX from FIG. 8.

FIG. 9 depicts a cut along the line IX-IX shown in FIG. 8.

The converter element layer sections 26 arranged on the inner side 34 each extend only across a centre point angle 35 of approximately 45°. A corresponding section of a bottom electrode 27 or a cover electrode 28 is assigned to each converter element layer section 26. A converter element layer 26 that extends across the entire circumference of the supporting body 25 is applied on the outer side of the supporting body 25 in the corresponding recess 31, again, accordingly, with bottom electrode 27 and cover electrode 28.

It is self-evident that the converter element layer 26 is also applied on the outer side of the supporting body 25, where appropriate, only in sections with correspondingly associated centre point angle, or that the converter element layer 26 extends across the entire circumference of the inner bore hole of the supporting body 25 on the inner side 34.

Furthermore, it is to be pointed out that also applying to the embodiment in accordance with FIGS. 8 and 9 are the characteristics for, for example, the support material, use of the pressure sensor as a washer, relationships of the corresponding moduli of elasticity or products of the modulus of elasticity and the area and the like portrayed in connection with FIGS. 1 to 7. Reference is made to the above description/embodiments in this regard.

For simplification, the electrical contact-connections conducted outwards from the bottom and cover electrodes 27, 28 are not shown in FIGS. 8 and 9.

Various possible applications are conceivable for the pressure sensor 1 according to the invention. In one possibility, the corresponding pressure sensor is built directly into a location at which a corresponding pressure or force is to be measured. This applies, for example, to pressure-sensitive material connections, such as, for example, on steel constructions that require precise frictional connections. The pressure sensor in this case is located between the materials that are to be joined, and can remain in this construction even after a corresponding screwed connection or the like has been tightened. During tightening, an exact evaluation of the pressure torques, and consequently the exact measurement of the frictional connection, is possible. The corresponding evaluation device is connected only temporarily and can be removed later. The evaluation device can be connected to the pressure sensor again at any time.

A further possible use is, for example, in electrode holders, in which, by means of two electrode holder arms, two welding electrodes are brought close to one another and pressed, from opposing sides, on to the parts that are to be welded. As a rule, the pressure at the time of the welding is specified relatively precisely, in order to set perfect weld points. This pressure can be determined by a correspondingly built-in pressure sensor. In the case of welding electrodes, there is furthermore the possibility that these no longer come together exactly for welding after multiple use or due to mechanical stress. In this case, forces arise that are perpendicular to the direction of the welding electrodes, whereby these forces can be determined, for example, by a pressure sensor according to FIG. 7 or 9.

Furthermore, the pressure increase and reduction in a corresponding welding device of the type described can be measured by such a pressure sensor.

A pressure sensor according to FIG. 7 or 9 can also be assigned to a corresponding mechanical connection without the use of the division into pressure measuring sectors, for example, in the manner of a washer, and can be used for the measurement of corresponding forces or pressure torques.

There is furthermore a possibility of producing the pressure sensor 1 according to the invention in customer-specific designs, according to the application area, whereby, in principle, such a corresponding design can be cut from a plate-shaped or disc-shaped pressure sensor 1. Use in various production systems, machine tools and the like is possible.

The arrangement of converter elements, support material and insulating material can also take place in various ways. An example is tubes as the support material, with inserted, rod-shaped converter elements that are arranged parallel in a composite component with a polymer as the insulating material. A further example is a slit ring as the support material, with slits in the axial direction and rod-shaped converter elements arranged in the slits.

The various arrangements of these elements can be described in principle by numerical notation that reflects the connectivity, whereby the corresponding numbers describe the dimensionality of the individual elements in the composite component.

In each case, the first number corresponds to the dimension number of the converter element, the second number corresponds to the dimension number of the support material and the last number corresponds to the dimension number of the insulating material. For example, the number group 1/2/3 indicates a rod-shaped converter element in a tube as support material, which are three-dimensionally cast by the insulating material. The number group 2/2/2 means plate-shaped converter elements parallel to plates as the support material, which are two-dimensionally glued by the insulating material. Given as an example is the further number group 1/2/1, whereby in this case, rod-shaped converter elements are arranged in tube slits or plate slits of the support material and one-dimensionally glued by the insulating material.

Various additional number groups are obvious.

The invention claimed is:

1. A pressure sensor with a multiplicity of piezoelectric converter elements, which are arranged such that a longitudinal dimension of the piezoelectric converter elements are substantially parallel to a force-applying or pressure-applying direction, and the piezoelectric converter elements are arranged at a distance from one another by an insulating material or are at least partially embedded in said insulating material, wherein the piezoelectric converter elements are electrically contact-connected by an electrical contact-connection, wherein a support material having greater mechanical rigidity in the force-applying or pressure-applying direction than the piezoelectric converter elements is assigned to a plurality of the piezoelectric converter elements, and wherein the support material assigned to the plurality of piezoelectric converter elements extends along at least one side of the plurality of piezoelectric converter elements substantially parallel to the force-applying or pressure-applying direction up to opposite free ends of the plurality of piezoelectric converter elements along the longitudinal dimension, wherein the force or the pressure is applied onto the free ends of the plurality of piezoelectric converter elements.

2. The pressure sensor according to claim 1, wherein the piezoelectric converter elements have a circular, rectangular, or oval cross-section.

3. The pressure sensor according to claim 1, wherein the piezoelectric converter elements are arranged in a matrix.

4. The pressure sensor according to claim 1, wherein the insulating material is a polymer material or glass.

5. The pressure sensor according to claim 1, wherein the electrical contact-connection is connected to the free ends of the piezoelectric converter elements.

6. The pressure sensor according to claim 1, wherein the electrical contact-connection is formed as a conductive coating as strip conductors.

7. The pressure sensor according to claim 1, wherein the electrical contact-connection is formed as a material that contains electrically conductive particles.

8. The pressure sensor according to claim 1, wherein the piezoelectric contact elements are cylindrical piezoelectric contact elements, with an annular surface of the cylindrical piezoelectric contact elements being the at least one side and opposite flat ends of the cylindrical piezoelectric contact elements being the free ends thereof, and the support material comprises a plurality of support tubes, each one of the support tubes having a central bore and holding one of the cylindrical piezoelectric converter elements within the central bore such that each support tube surrounds the side of one of the cylindrical piezoelectric contact elements.

9. The pressure sensor according to claim 8, wherein each one of the cylindrical piezoelectric converter elements is arranged uniaxially together with one of the support tubes.

10. The pressure sensor according to claim 1, wherein the piezoelectric contact elements are rod-shaped piezoelectric contact elements, and the support material has a multiple number of support rings, each of which can hold at least one of the rod-shaped piezoelectric converter elements.

11. The pressure sensor according to claim 1, wherein the piezoelectric contact elements are plate-shaped piezoelectric contact elements, and the support material has a multiple number of support plate pairs, wherein each pair holds one of the plate-shaped piezoelectric converter elements between them.

12. The pressure sensor according to claim 1, wherein the piezoelectric converter elements and the support material form a composite material with the insulating material.

13. The pressure sensor according to claim 1, wherein the piezoelectric converter elements and the assigned support material are cast with the insulating material.

14. The pressure sensor according to claim 1, wherein the support material is a solid material with a multiplicity of corresponding receptacles, each for one of the piezoelectric converter elements.

15. The pressure sensor according to claim 1, wherein the piezoelectric converter elements and the support material are glued to each other by the insulating material.

16. The pressure sensor according to claim 1, wherein the support material is a ceramic material or a hard metal.

17. The pressure sensor according to claim 1, wherein the support material is aluminium oxide, aluminium nitride or another ceramic material with predominantly ionic bonding.

18. The pressure sensor according to claim 1, formed as a disc.

19. The pressure sensor according to claim 1, wherein a modulus of elasticity of the support material is greater than a modulus of elasticity of the piezoelectric converter elements.

20. The pressure sensor according to claim 1, wherein an insulating resistance of the support material is greater than an insulating resistance of the piezoelectric converter elements.

21. The pressure sensor according to claim 1, wherein the pressure sensor is divided into pressure measuring sectors substantially perpendicular to the force-applying or pressure-applying direction in a plane.

22. The pressure sensor according to claim 21, wherein each pressure measuring sector is arranged in the form of circular-segments around a centre axis of the pressure sensor, said centre axis being parallel to the force-applying or pressure-applying direction.

23. The pressure sensor according to claim 22, wherein each pressure measuring sector extends across a same centre point angle.

24. The pressure sensor according to claim 1, wherein the piezoelectric converter elements are formed from a ferroelectric piezoelectric material.

25. The pressure sensor according to claim 1, wherein the support material extends along the at least one side of the plurality of piezoelectric converter elements up to the opposite free ends thereof, but terminates at the opposite free ends.

26. A pressure sensor with at least one piezoelectric converter element which is electrically contact-contacted by an electrical contact-connection, wherein the at least one piezoelectric converter element is applied, in the form of a layer, to a supporting body made from a support material and the electrical contact-connection is made by a bottom electrode arranged between the layer and the supporting body, and a cover electrode which is applied to an outer side of the layer, wherein the support material has greater mechanical rigidity than the at least one piezoelectric converter element in the force-applying or pressure-applying direction, and wherein the support material extends along at least one side of the at least one piezoelectric converter element substantially parallel to the force-applying or pressure-applying direction up to opposite free ends of the at least one piezoelectric converter element along a longitudinal dimension thereof.

27. The pressure sensor according to claim 26, wherein the layer is applied to an outer side or an inner side of the supporting body.

28. The pressure sensor according to claim 27, wherein the layer extends up to the upper or lower side of the supporting body.

29. The pressure sensor according to claim 26, wherein the layer is arranged in a recess formed in an outer side or inner side of the supporting body and ends at a distance from the upper or lower side of the supporting body.

30. The pressure sensor according to claim 26, wherein a polarization of the layer is effected perpendicularly to the force-applying or pressure-applying direction by the bottom and cover electrodes.

31. The pressure sensor according to claim 26, wherein the support material extends along the at least one side of the at least one piezoelectric converter element up to the opposite free ends thereof, but terminates at the opposite free ends.

* * * * *